United States Patent
Lemer

(10) Patent No.: US 11,045,155 B2
(45) Date of Patent: Jun. 29, 2021

(54) MOVABLE RADIATION PROTECTION SCREEN

(71) Applicant: LEMER PAX, La Chapelle sur Erdre (FR)

(72) Inventor: Pierre-Marie Lemer, Nantes (FR)

(73) Assignee: LEMER PAX, La Chapelle sur Erdre (FR)

( * ) Notice: Subject to any disclaimer, the term of this patent is extended or adjusted under 35 U.S.C. 154(b) by 11 days.

(21) Appl. No.: 16/470,018

(22) PCT Filed: Dec. 13, 2017

(86) PCT No.: PCT/FR2017/053547
§ 371 (c)(1),
(2) Date: Jun. 14, 2019

(87) PCT Pub. No.: WO2018/109380
PCT Pub. Date: Jun. 21, 2018

(65) Prior Publication Data
US 2020/0100736 A1    Apr. 2, 2020

(30) Foreign Application Priority Data
Dec. 14, 2016   (FR) ...................................... 1662400

(51) Int. Cl.
*A61B 6/10* (2006.01)
*G21F 3/00* (2006.01)

(52) U.S. Cl.
CPC ............... *A61B 6/107* (2013.01); *G21F 3/00* (2013.01)

(58) Field of Classification Search
CPC ... A61B 6/107; G21F 1/00; G21F 1/12; G21F 1/125; G21F 3/00; G21F 7/00
See application file for complete search history.

(56) References Cited

U.S. PATENT DOCUMENTS

| 3,308,297 A | 3/1967 | Mansker |
| 8,445,093 B2 | 5/2013 | Lemer |

(Continued)

FOREIGN PATENT DOCUMENTS

| CN | 101 916 606 | 12/2010 |
| FR | 2915868 | 11/2014 |

(Continued)

OTHER PUBLICATIONS

International Search Report, PCT/FR2017/153547, dated Mar. 7, 2018.

*Primary Examiner* — David E Smith
(74) *Attorney, Agent, or Firm* — Nixon & Vanderhye

(57) ABSTRACT

Disclosed is a radiation protection screen for protecting an operator from ionizing radiation, which screen includes a front partition structure that is made of one or more radiation protection materials and a side partition structure that is made of one or more radiation protection materials, the partitions being joined together at a vertical or substantially vertical corner border, and which screen includes feet that are equipped with wheels that rest on the ground. Furthermore, according to the invention, this screen is arranged such that the front partition structure includes a lower portion and an upper portion that may be moved with respect to each other, the upper portion of the front partition structure being mounted so as to be able to pivot in the region of the corner border, about a vertical or substantially vertical pivoting axis.

15 Claims, 7 Drawing Sheets

(56) References Cited

U.S. PATENT DOCUMENTS

| | | | | |
|---|---|---|---|---|
| 2005/0173658 A1* | 8/2005 | Lemer | ................... | A61B 6/107 |
| | | | | 250/515.1 |
| 2006/0076522 A1 | 4/2006 | Goldstein | | |
| 2007/0252095 A1* | 11/2007 | Magram | ................... | G21F 3/00 |
| | | | | 250/515.1 |
| 2008/0073593 A1* | 3/2008 | Fox | .......................... | G21F 3/00 |
| | | | | 250/503.1 |
| 2010/0304060 A1* | 12/2010 | Lemer | ................ | A61B 6/4423 |
| | | | | 428/34.1 |
| 2012/0049093 A1 | 3/2012 | Costea | | |
| 2015/0206609 A1* | 7/2015 | Lemer | ................... | A61B 6/107 |
| | | | | 250/515.1 |

FOREIGN PATENT DOCUMENTS

| | | |
|---|---|---|
| JP | 2001-120543 | 5/2001 |
| WO | WO 2009/156660 | 12/2009 |

* cited by examiner

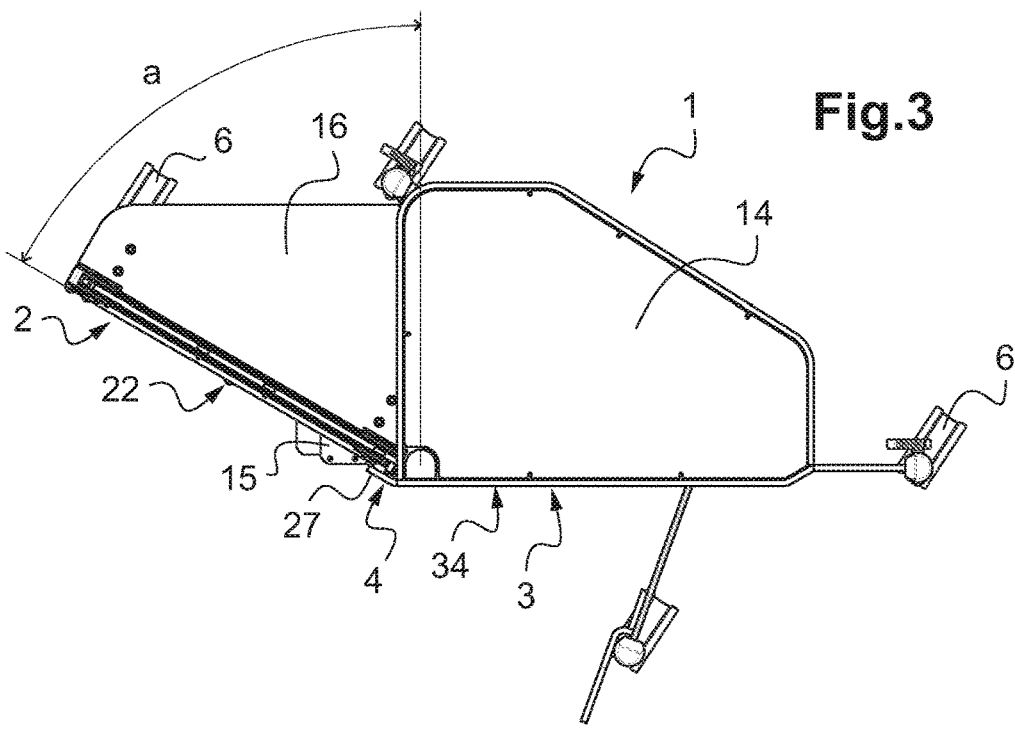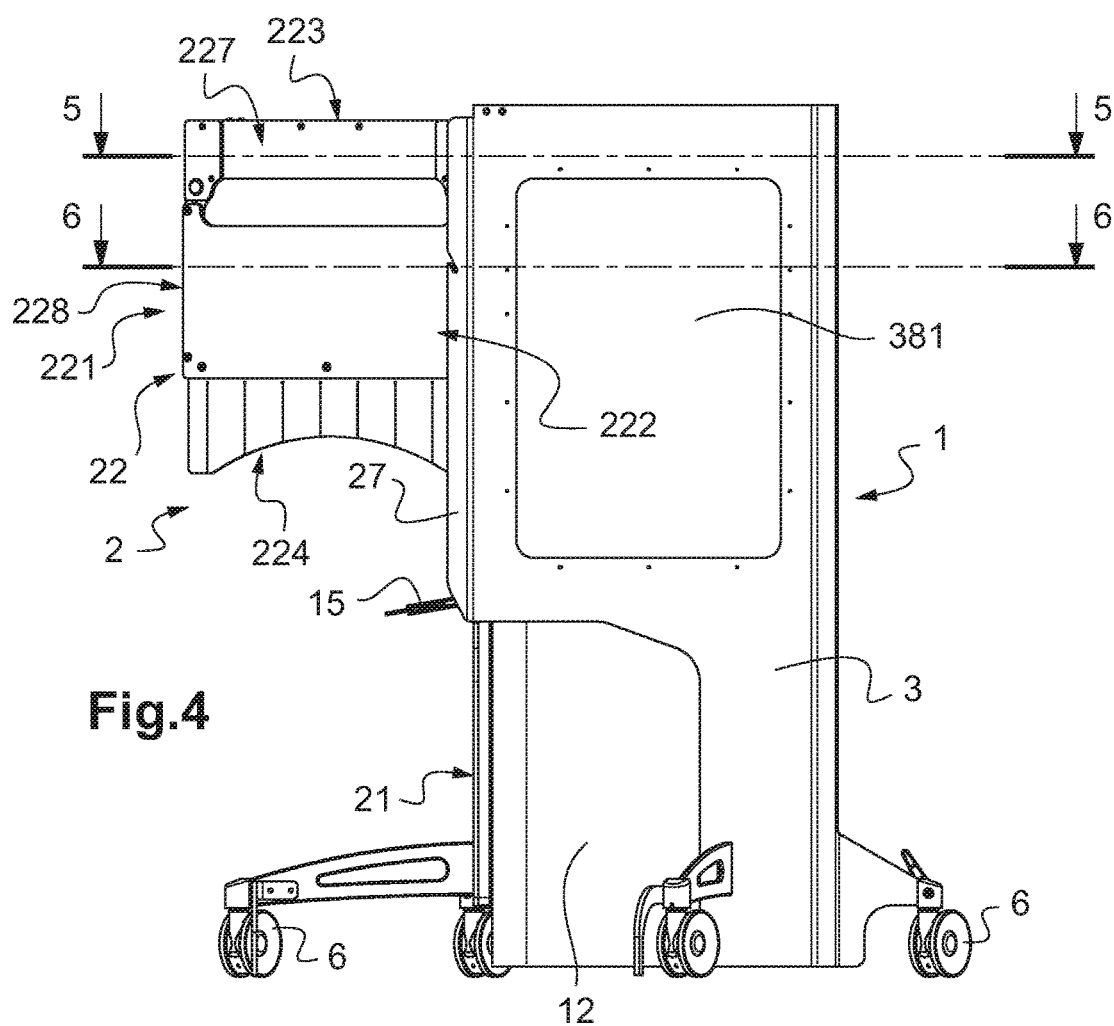

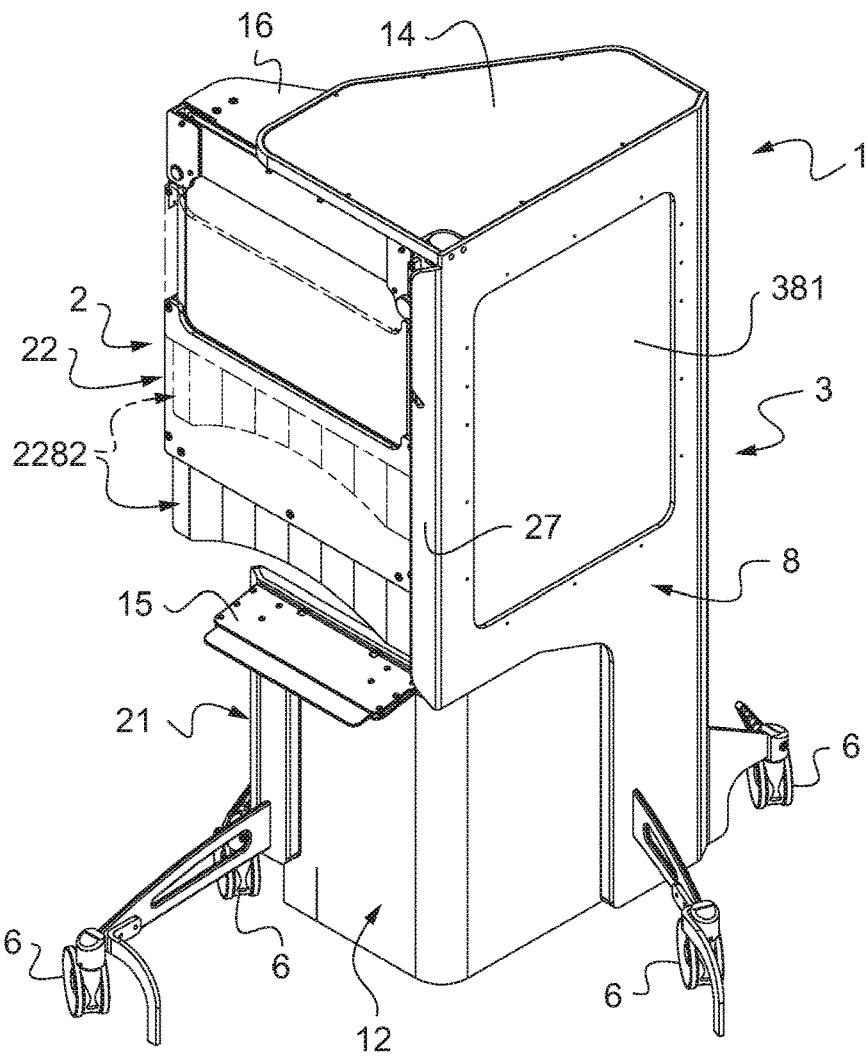
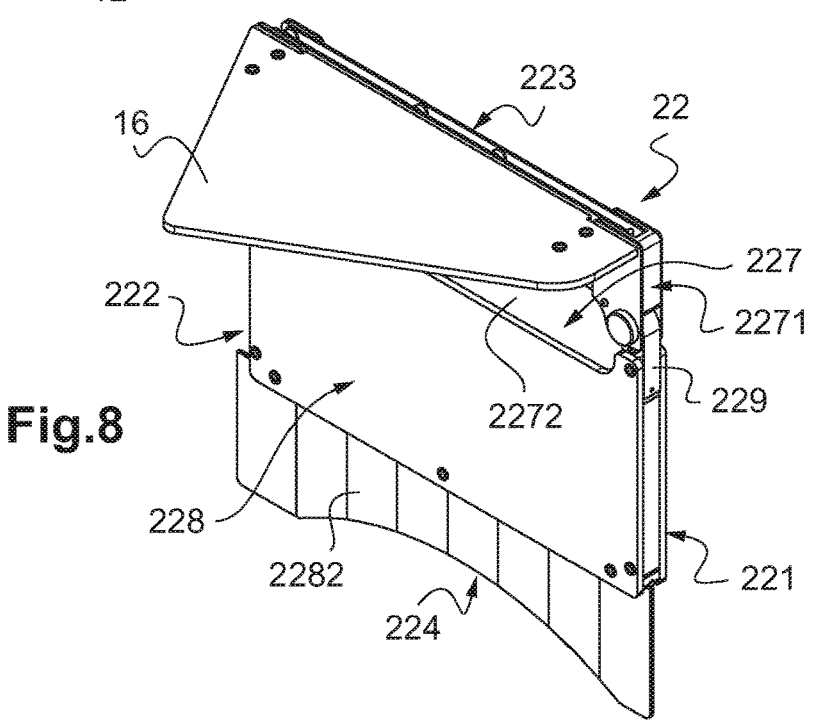

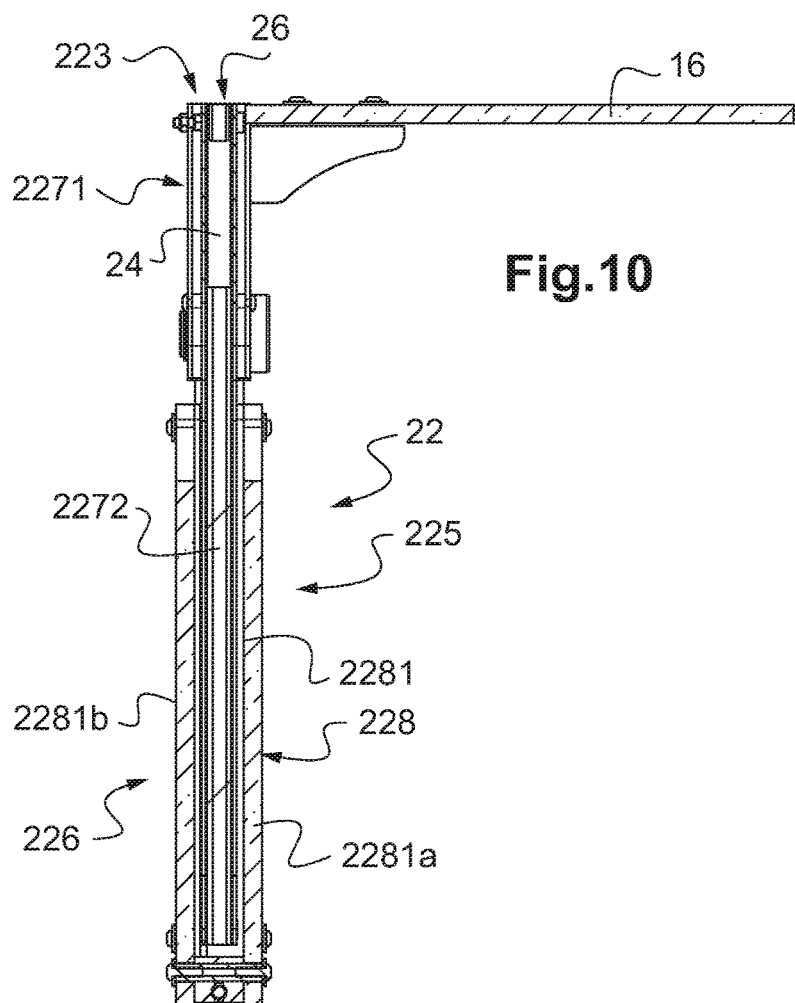
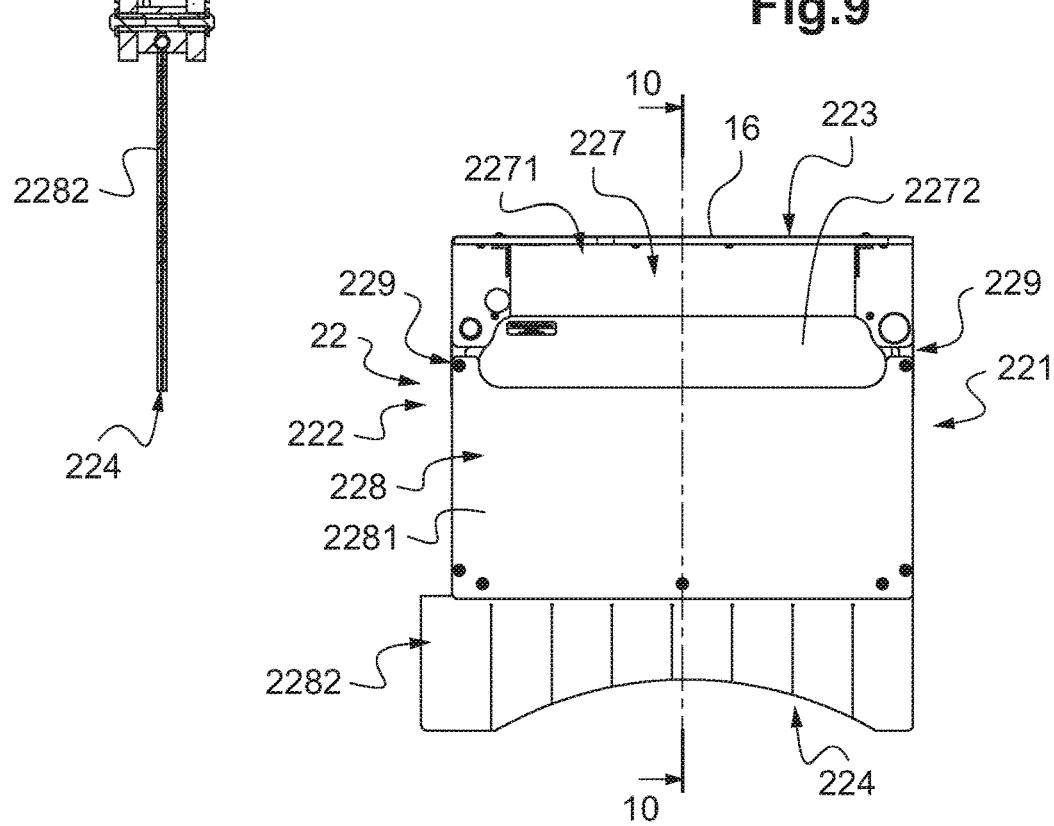

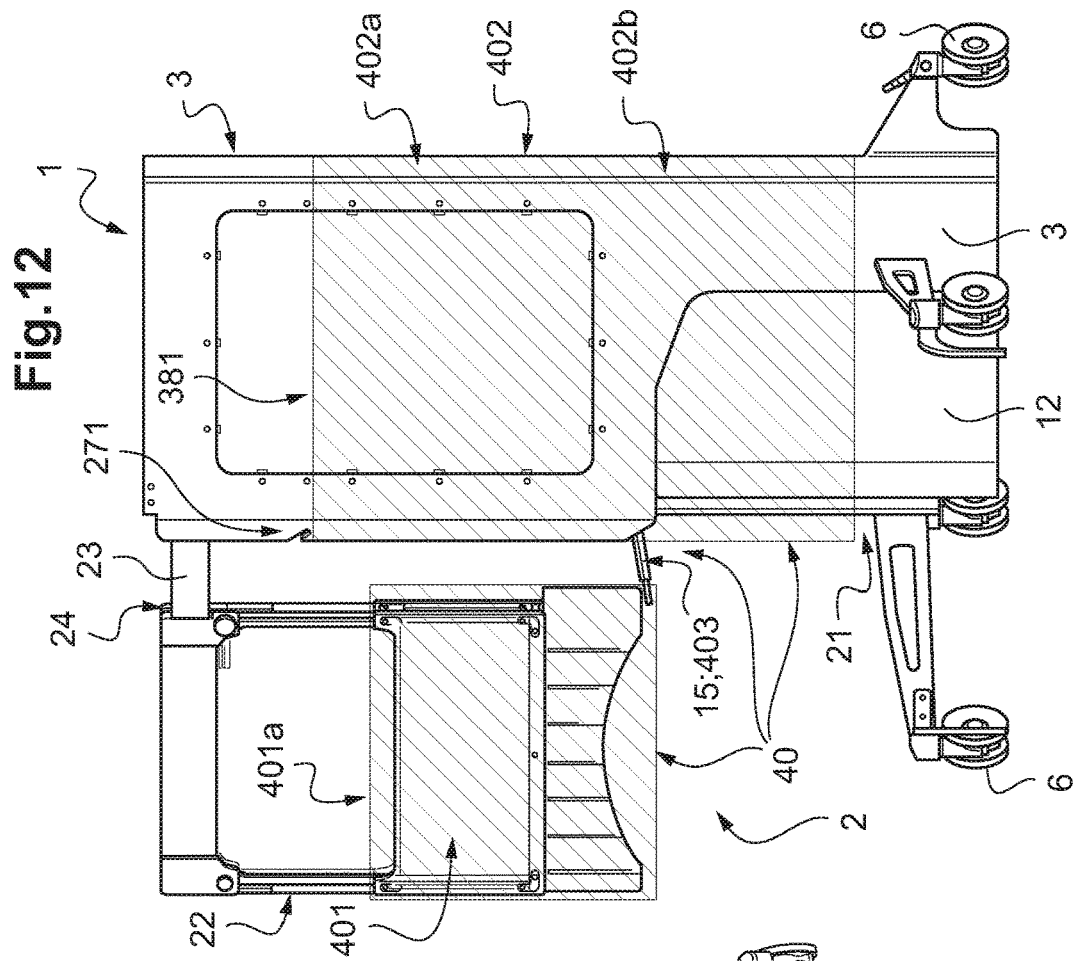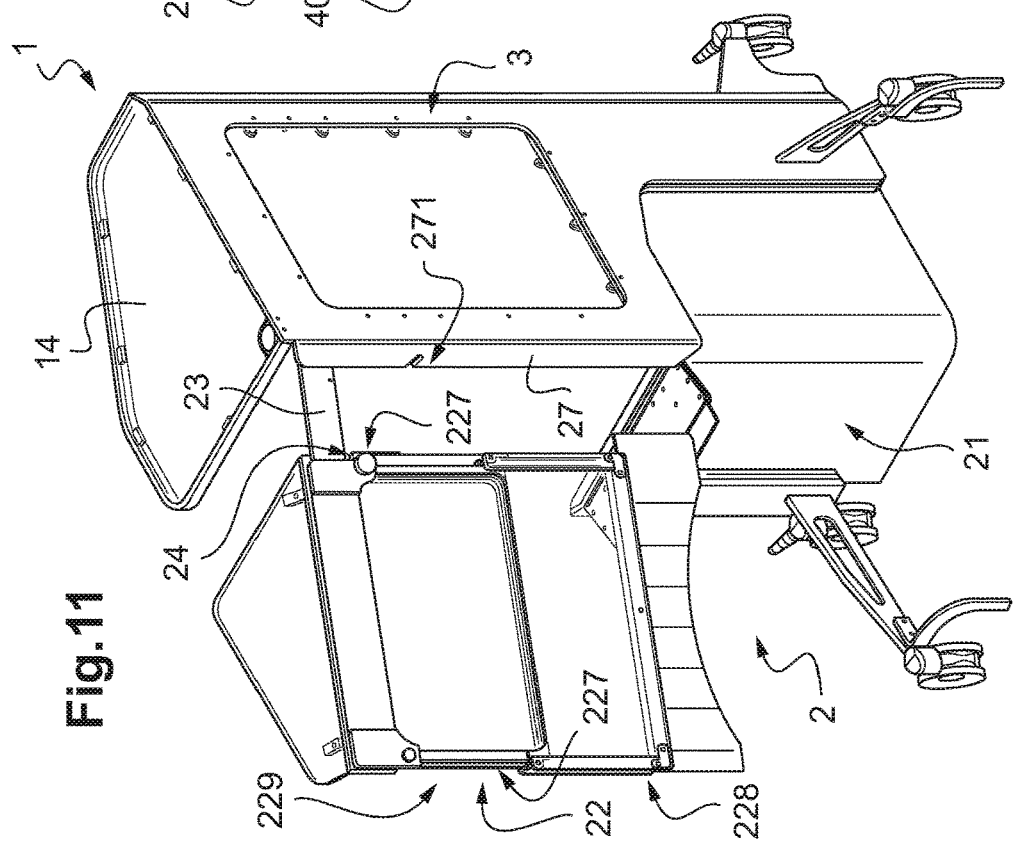

MOVABLE RADIATION PROTECTION SCREEN

TECHNICAL FIELD THAT THE INVENTION IS RELATED TO

The present invention is generally related to the field of equipment for protection from ionizing radiation.

It is especially related to radioprotective screens which are used in the medical field or other fields for protecting an operator from the emission of ionizing radiation such as X-rays. It is also related to a cover-shaped equipment for wrapping such screens by covering them for the purpose of using them in a sterile protected environment.

TECHNICAL BACKGROUND

During certain examinations or interventions, the patients are exposed to ionizing radiation, especially of the X-rays type, which are used for checking, for diagnostic or for treatment.

That is particularly the case for interventions such as catheterization, installing pacemakers, vascular, neurological or urological examinations, CIM (Cardiac Rhythm Management), CRT (Cardiac Resynchronization Therapy) or during application of fluoroscopy techniques.

Particularly, fluoroscopy is an imaging technique which consists in using X-rays for obtaining real-time images of an object. In the medical field, applying this technique allows the visualization of structures and functions of the internal organs of a patient, such as, for example, the heartbeat or the blood flow in the blood vessels. That technique is used for diagnostic as well as for therapy; and it is used in the intervention fields especially of radiology, cardiology, neurology, electrophysiology, peripheral vascular radiology, pediatric intervention, . . .

The rooms dedicated to these specialties are equipped with fluoroscopic appliances (also called C-arms) which are conceived with the general shape of a movable technical case having an extension formed by a large arch with one end carrying an X-ray emitting device and the other end being provided with a detector.

In the equipped rooms, catheters and probes are introduced into an access (generally the femoral or the radial artery) for the purpose of diagnostic or therapy.

The vascular system is visualized by using X-rays, often together with injection of contrast product(s).

These fluoroscopy appliances occupy an important space around the examination table and their positioning is often changed as a function of the body region of the patient to examine or to treat.

It will be understood that it is important to properly protect the operators (doctors, surgeons, technicians, nurses, and others) from the emitted ionizing radiation (of the primary type coming directly from the emitter, or of the secondary type reflected by the appliances or coming directly from the patient) in order to avoid exposing them to important doses as accumulated over the time and liable to generate different diseases (necroses of the upper members, brain tumors, cataracts, radiodermatitis, and so on).

To this end, protective structures exist which consist of clothes such as blouses, chasubles, aprons made of radioprotective material, thyroid protections, glasses, . . . , but which do not always cover the entire body, and whose important weight is detrimental to the operator's comfort, limits his ability to move and entails a rapid fatigue.

There also are screens or shields consisting of panels or assemblies of panels made of appropriate radioprotective material, hanging on an adapted support or lying on the floor either directly or by means of a rolling base.

Such structures of radioprotective screens are described in documents US-2012/0049093, US-2006/0076522, FR-2 915 868, WO-2009/156660, and further U.S. Pat. No. 3,308,297.

However, those different structures do not allow an operator to work under optimal conditions. Especially, certain ones of them are not well adapted for allowing an operator situated on the protected side of the screen to get with his arms or his hands to the other side of that screen, for example in order to intervene on a part of the patient's body that is exposed to the radiation.

Further, the structures of screens known up to now, often reveal as being inconvenient for moving the appliances of the operating room, especially the fluoroscopic appliances.

OBJECT OF THE INVENTION

In order to overcome the above mentioned disadvantages of the state of the art, the present invention proposes a radioprotective screen for protecting at least one operator from ionizing radiation, said screen being of the type of comprising a front wall structure made of radioprotective material(s), and a lateral wall structure made of radioprotective material(s), linked to one another at a vertical or essentially vertical corner edge, said screen comprising a base provided with ground support wheels;

and according to the invention, said front wall structure comprises a lower part and an upper part which are movable relative to one another, said upper part of said front wall structure being mounted pivotally around a vertical or essentially vertical pivoting axis at said corner edge.

By its front wall structure positioned directly in front of an examination table on which a patient is lying, such a screen allows to protect the operator efficiently while leaving to him a large freedom of movements. The pivoting movable upper part of the front wall structure can be moved by the operator to the side or above the patient according to the action to be performed; and in case of contact with surrounding appliances, for example the fluoroscopic C-arm, that movable upper part can pivot, thus avoiding to move the whole screen.

Other not limiting and advantageous characteristic features of the radioprotective screen according to the invention, as considered individually or in any technically possible combination, are the following ones:

the lateral wall structure extends in a vertical or essentially vertical plane and comprises: —a free lateral edge, —a lateral edge defining a part of said corner edge, —a lower edge, and—an upper edge, said lateral wall structure comprising an upper part, at least a part of which is made of a transparent radioprotective material, and a lower part, and the lower part of the front wall structure is defined by: —a free lateral edge, —a lateral edge defining a part of said corner edge, —a lower edge, and—an upper edge, said lower part of the front wall structure extending in a vertical or essentially vertical plane which is offset with respect to the plane of said lateral wall structure by a fixed angle between 70 and 120°, preferably in the order of 90°.

The screen comprises a part made of flexible radioprotective material which is shaped as a panel that extends over a part of the height of said corner edge, and over a part of said lower part of the lateral wall structure as well as over a part of the lower part of the front wall structure at both sides of said corner edge.

More precisely, said panel made of flexible radioprotective material advantageously extends a) from the lower edge of said lower part of the lateral wall structure, and from the lower edge of the lower part of the front wall structure over more than half of the height of said lower parts of the lateral wall structure and of the front wall structure, and b) from said corner edge over more than half of the width of said lower parts of the front and lateral wall structure.

The lateral wall structure comprises an inner face turned towards the positioning space of the operator, and an opposite outer face; and the upper edge of the lateral wall structure comprises an extension forming a roof made of radioprotective material, which extends on the side of said inner face.

The lower part of the front wall structure comprises: an inner face turned towards the positioning space of the operator, an opposite outer face, and an upper edge; and said upper edge comprises a protective extension made of radioprotective material which extends on the side of said outer face; that protective extension can be shaped as a tablet that extends in a horizontal or essentially horizontal position from the upper edge of the lower part of the front wall structure; it is advantageously mounted pivotally on said upper edge of the lower part of the front wall structure, in order to allow it to be raised from said horizontal position; and it comprises advantageously a retractable end extension for making it telescopic;

in a variant embodiment, that protective extension can consist of a semi-rigid bib which extends upward from the upper edge of the lower part of the front wall structure and has a circular-arc or essentially circular-arc shaped cross-section.

The upper part of the front wall structure comprises a free lateral edge, a lateral edge forming a part of the corner edge, an upper edge, a lower edge, an inner face turned towards the positioning space of the operator, and an opposite outer face; further, it is formed by at least one panel made of radioprotective material.

The lateral edge of the lateral wall structure, which forms a part of said corner edge, comprises an extension shaped as a lateral wing adapted to cover the lateral edge which is in front of the upper part of the front wall structure, and the associated pivoting axis, the cover being formed on the side of the outer face of the upper part of the front wall structure.

The upper edge of the upper part of the front wall structure comprises a roof-forming extension made of radioprotective material which extends on the side of the inner face of said upper part of the front wall structure in a plane that is offset with respect to the plane of the roof-forming extension of the lateral wall structure.

The lower edge of the upper part of the front wall structure is formed by a flexible curtain composed by a juxtaposition of a plurality of flexible bands made of radioprotective material.

The upper part of the front wall structure comprises an upper panel at least a part of which is made of radioprotective material, and a lower panel at least a part of which is made of a transparent radioprotective material, said lower panel being vertically translationally movable with respect to said upper panel, in order to form a telescopic upper part of the front wall structure, the height of which can be adjusted;

advantageously, the movable lower panel is attached to said upper panel by means of an equilibrium system, e.g. of the spiral-spring type with constant force.

The upper part of the front wall structure comprises a supporting arm pivotally mounted on said corner edge around said pivoting axis, and said at least one panel forming the upper part is movably mounted on said supporting arm for horizontal translational movement.

The invention further proposes a cover-shaped equipment intended for covering at least part of the height of a radioprotective screen as defined here above, said equipment comprising:

a flexible pocket provided with an opening, said flexible pocket being able to cover at least partially the upper part of the front wall structure by entering the lower edge of the latter into the opening of said flexible pocket, said flexible pocket being provided with at least one transparent part and with means for fixing it to said upper part of the front wall structure, and at least one flexible panel able to cover at least partially said lateral wall structure and the lower part of said front wall structure, said at least one flexible panel comprising at least one transparent part intended for being positioned in front of the transparent part of said lateral wall structure, and fixing means on said lateral and front wall structures, and when it comprises a protective extension which extends the upper edge of the lower part of the front wall structure, a flexible structure covering said protective extension at least partially, either fixed to said panel for covering said lateral wall structure and the lower part of the front wall structure, or independent from said panel, said flexible structure being provided with means for fixing it to said tablet.

DETAILED DESCRIPTION OF AN EXEMPLARY EMBODIMENT

The following description with reference to the enclosed drawings which are enclosed as not limiting examples, will make understand well what the invention consists of and how it can be carried out.

On the enclosed drawings

FIG. 3 is a view from above the radioprotective screen represented on FIGS. 1 and 2;

FIG. 4 is a side view of the radioprotective screen represented on FIGS. 1-3;

FIG. 7 is a perspective view of the radioprotective screen of FIGS. 1-6, shown with another configuration of the upper part of its front wall structure (i.e. situated in the plane of the lower part of the front wall structure);

FIG. 8 is a perspective view of the separately shown upper part of the front wall structure of the radioprotective screen of FIGS. 1-7;

FIG. 9 is a front view of the upper part of the front wall structure represented on FIG. 8;

FIG. 10 is a sectional view according to plane 10-10 of FIG. 9;

FIG. 11 is a perspective view of the radioprotective screen of FIG. 7, shown with still another configuration of the upper part of its front wall structure, adapted for being provided with an equipment shaped as a sterile cover, in view of being used in an operating room;

FIG. 12 is a side view of the protective screen of FIG. 11, showing the equipment shaped as a cover as being placed on its different receiving parts;

Figure 1:
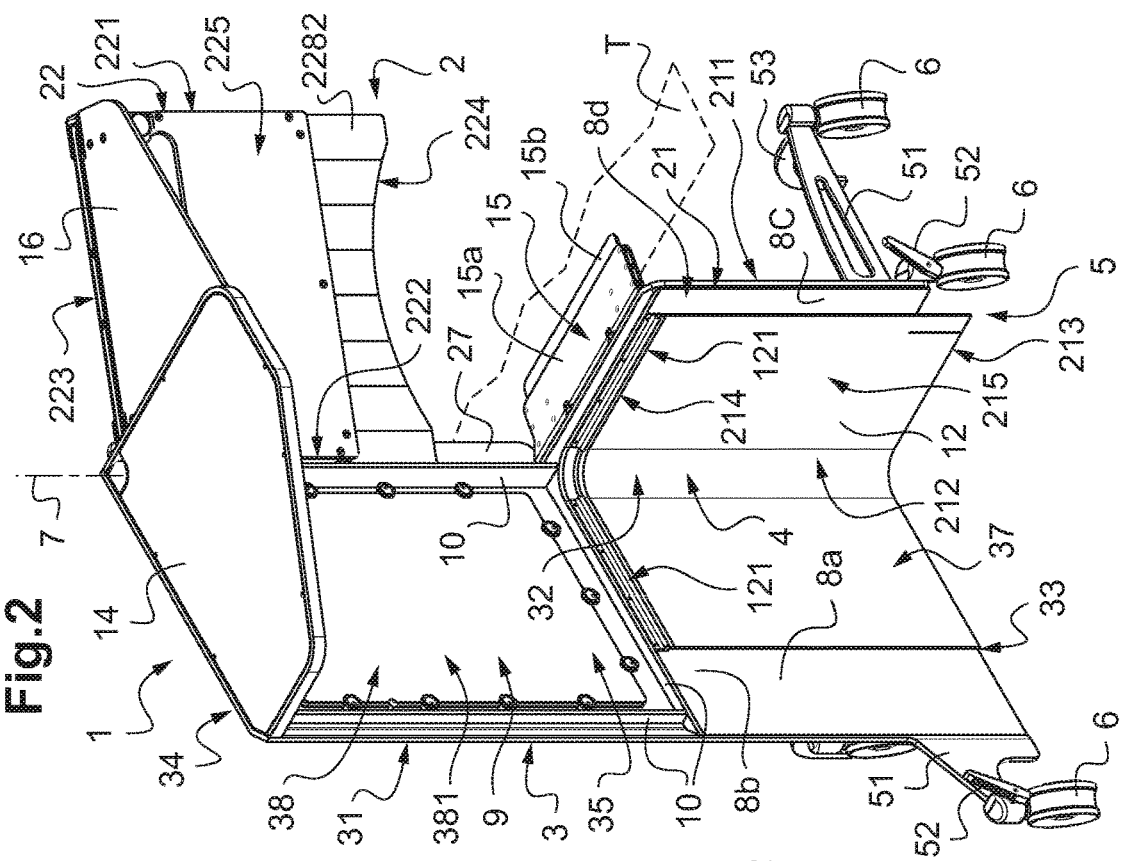
FIG. 1 shows a radioprotective screen according to the invention as a perspective view from the outer face (opposite to the positioning space of the operator, the upper part of the front wall structure being angularly offset with respect to the lower part of said front wall structure.

The radioprotective screen 1 shown on FIGS. 1-12 is adapted for assuring the protection of an operator from ionizing radiation emitted by a source of ionizing radiation, for example X-rays emitted by a fluoroscopic appliance of the C-arm type, in an operating room of a hospital.

To this end, the different parts forming this radioprotective screen 1 are made of radioprotective material(s) having an adapted lead equivalence, of at least 0.2 mm, according to the respective constituent parts. For example, that lead equivalence is comprised between 0.5 mm and 3 mm.

Such as shown on FIGS. 1-7, the radioprotective screen 1 has the shape of a movable cabin comprising a front wall structure 2 made of radioprotective material(s) and a lateral wall structure 3 made of radioprotective material(s), attached to one another at a vertical or essentially vertical corner edge 4, the whole being mounted on a base 5 provided with ground support wheels 6.

The lateral wall structure 3 has the shape of a panel that extends in a vertical or essentially vertical plane; and the front wall structure 2 has two parts:
  a lower part 21 which is fixed with respect to the lateral wall structure 3 and which extends in a vertical or essentially vertical plane, and
  an upper part 22 which also extends in a vertical or essentially vertical plane and which is mounted pivotally mound a vertical or essentially vertical pivoting axis 7 at the corner edge 4, above the lower part 21.

Thus, that upper part 22 is movable with respect to the lateral wall structure 3; and it also is movable with respect to the lower part 21, above the latter.

The lateral wall structure 3 comprises:
a free lateral edge 31,
a lateral edge 32 defining a part of said corner edge 4,
a lower edge 33,
an upper edge 34,
an inner face 35 turned towards the space dedicated to the positioning of the operator,
an outer face 36 opposite the inner face 35,
a lower part 37, and
an upper part 38, at least a part 381 of which is made of transparent radioprotective material.

The lower part 37 and the upper part 38 extend as an extension of one another, the horizontal lower edge 381' of the transparent part 381 forming, by definition, the separating line between said upper 38 and lower 37 parts (and forming thus the lower edge of the upper part 38 and the upper edge of the lower part 37). The height of the upper part 38 can be in the same order as the height of the lower part 37.

The lower part 21 of the front wall structure 2 is delimited by
a free lateral edge 211,
a lateral edge 212 defining a part of the corner edge 4,
a lower edge 213, and
an upper edge 214.

Said lower part 21 of the front wall structure 2 further comprises an inner face 215 turned towards the space intended for the positioning of the operator, and an outer face 216, opposite the inner face 215; and said lower part 21 extends in a vertical or essentially vertical plane which is offset with respect to the plane of said lateral wall structure 3 by a fixed angle, here 90°, as seen from the side of said inner faces 215 and 35.

In variants of that embodiment, said fixed angle can be different, for example between 70 and 120°.

The lateral wall structure 3 and the lower part 21 of the front wall structure 2 comprise one or more parts made of radioprotective material such as lead, steel, cast-iron, for example, having a lead equivalence of at least 0.2 mm, forming a frame 8 of the screen 1, on the lower part of which ground support wheels 6 are mounted, forming the base 5.

These wheels 6, at least three ones, here four ones, are mounted to the frame 8 by means of arms 51.

At least some of the wheels 6 are provided with a locking lever 52 for avoiding temporarily their rotation (for example the wheels 6 accessible from the inner side of screen 1); and at least certain ones of the wheels 6 are provided here with an anti-tilt foot 53 (for example the wheels accessible from the outer side of screen 1). In a variant of the embodiment, these anti-tilt feet 53 may be omitted.

One part of the wheels 6 is provided on the lower part 37 of the lateral wall structure 3 and another part of these wheels 6 is provided on the lower part 21 of the front wall structure 2.

A large central opening 9 is provided in the part of the frame 8 that corresponds to the upper part 38 of the lateral wall structure 3, for receiving a transparent panel forming the above-mentioned part 381 made of transparent radioprotective material. This panel 381 can be made of lead-containing plastic material of the type "Kyowaglass" (registered trade mark), radioprotective plastic material of the type "Novashield glass" (registered trade mark), lead-containing glass, or others, all having a lead equivalence comprised between 0.2 mm and 3 mm. It is mounted on the periphery of opening 9, on the side of the inner face 35, by any appropriate means that protects from ionizing radiation. Said transparent panel 381 extends roughly over the entire width and roughly over the entire height of the upper part 38 of the lateral wall structure 3. It has a rectangular shape in the order of 60 cm wide and 80 cm high.

Stiffening profiles 10 are provided on at least a part of the periphery of the central opening 9 in order to improve the characteristics of resistance/stiffness of the frame 8 of the radioprotective screen 1.

Figure 2:
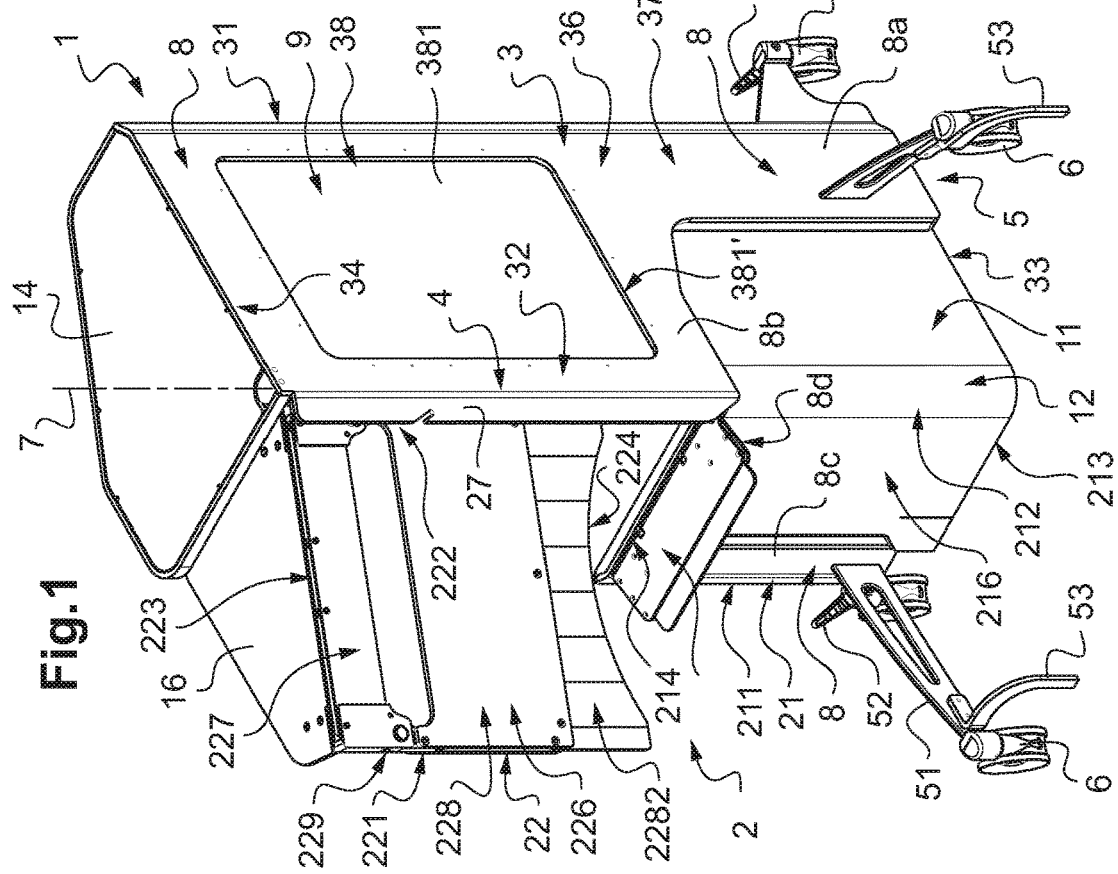
FIG. 2 shows the radioprotective screen of FIG. 1 as a perspective view from the inner face, i.e. from the side of the positioning space of the operator.

On FIGS. 1 and 2, it can be seen that the lower part of frame 8 of the screen 1 comprises a large opening 11 allowing for passing an equipment such as an end part of a fluoroscopic C-arm, that opening 11 being filled by a panel 12 made of flexible radioprotective material and capable to distort by contact with said equipment and forming at the same time a barrier against ionizing radiation.

The opening 11 and thus the panel 12 made of flexible radioprotective material, extend at the lower part of the corner of the screen 1, i.e. they extend, from the corner edge 4 and the lower edges 33 and 213: over a part of the height and the width of the lower part 37 of the lateral wall structure 3, as well as over a part of the height and the width of the lower part 21 of the front wall structure 2.

More precisely, the opening 11 and the panel 12 made of flexible radioprotective material extend:

from the lower edge 33 of the lower part 37 of the lateral wall structure 3 and the lower edge 213 of the lower part 21 of the front wall structure 2, over more than half of the height of said lower parts 37 and 21 of the lateral wall structure 3 and the front wall structure 2, and from the corner edge 4 over more than half of the width of said lower parts 37 and 21 of the front 2 and lateral 3 wall structures.

On the lower part 37 of the lateral wall structure 3, the frame 8 thus comprises a lateral strip 8a on which certain ones of the arms 51 of the ground support wheels 6 are mounted, and an upper strip 8b.

On the other hand, on the lower part 21 of the front wall structure 2, the frame 8 comprises a lateral strip 8c on which certain ones of the arms 51 of the ground support wheels 6 are mounted, and an upper strip 8d.

The panel 12 made of radioprotective material is fixed by its upper edge 121 on the upper strips 8b and 8d of the frame 8 (i.e. near the upper edges 214 and 381' of the lower parts 21 and 37) on the side of the inner faces 215 and 35 of the front 2 and lateral 3 wall structures. The vertical edges of this flexible panel 12 are left free or are fixed to the frame 8 by elastic means, allowing this panel 12 to distort especially towards the interior of the screen 1.

The dimensions of the panel 12 made of flexible radioprotective material are a bit greater than the ones of the opening 11 in order to allow a slight overlapping at the upper part and at the sides, for fulfilling the protective function looked for.

The panel 12 can be formed by one or by several sheets of PVC or of flexible rubber, both containing lead or another radioprotective material, all having a lead equivalence of at least 0.20 mm.

As a variant, the panel 12 can be replaced by a juxtaposition of vertical bands made of radioprotective material, for example one-piece bands made of flexible material, or bands made by assembling rigid elements linked two by two by an articulation.

As can be seen on FIGS. 1 to 3, the upper edge 34 of the lateral wall structure 3 comprises an extension 14 forming a roof made of radioprotective material, which extends on the side of the inner face 35. Here, that extension 14 extends square with respect to the plane of the lateral wall structure 3 and over the whole width of the upper edge 34; advantageously it is made of radioprotective material, for example of lead-containing plastic, of the type "Kyowaglass" (registered trademark), radioprotective plastic of the type "Novashield glass" (registered trademark), lead-containing glass, or others, all having a lead equivalence comprised between 0.2 mm and 3 mm.

The upper edge 214 of the lower part 21 of the front wall structure 2 comprises an extension having the shape of a tablet 15 made of radioprotective material which extends on the side of the outer face 216.

This tablet extends from the upper edge 214 in a horizontal or essentially horizontal position, i.e. perpendicularly or essentially perpendicularly to the vertical plane of the lower part 21 of the front wall structure 2; it comprises advantageously a rigid base 15a which is extended by a retractable rigid end extension 15b, in order to make it telescopic and thus be able to adapt its length.

Advantageously, the tablet 15 is pivotally mounted on the upper edge 214 of the lower part 21 in order to allow it to be raised from said horizontal stability position.

That possibility of raising is interesting, for example for avoiding to raise the screen 1 or to trap the patient in case the examination table, on which the patient is lying, is raised.

The base part 15a and the end extension part 15b of the tablet 15 can, for example, be made of stainless steel having a lead equivalence of at least 0.20 mm.

As a variant, the tablet 15 can be foreseen as not being telescopic and can be made of flexible or semi-flexible material.

The upper part 22 of the front wall structure 2 is pivotally mounted around the vertical pivoting axis 7, at the corner edge 4, above the upper edge 214 of the lower part 21 of the front wall structure 2.

That pivoting upper part 22 is delimited by
a free lateral edge 221,
a lateral edge 222 forming a part of the corner edge 4,
an upper edge 223,
a lower edge 224,
an inner face 225 turned towards the positioning space of the operator, and
an opposite outer face 226.

And further, this pivoting upper part 22 is formed by an upper panel 227 associated with a lower panel 228, said lower panel 228 being vertically translationally movable with respect to said upper panel 227, in order to form a telescopic upper part 22 of the front wall structure 2, the height of which can be adjusted.

As can be seen on FIGS. 8-10, the upper panel 227 comprises an upper part 2271 at least partially made of a metallic radioprotective material such as steel having a lead equivalence of at least 0.20 mm, extended-downwards by a lower part 2272 made of transparent radioprotective material, for example formed by a panel made of lead-containing plastic, of the type "Kyowaglass" (registered trademark), radioprotective plastic of the type "Novashield glass" (registered trademark), lead-containing glass, or others, all having a lead equivalence comprised between 0.2 mm and 3 mm. Metal edging profiles are provided on the lower edges of that lower part 2272, and on the lateral edges of that lower part 2272, between the upper part 2271 and said lower edge.

The lower panel 228 comprises itself an upper part 2281, extended downwards by a lower part 2282.

The upper part 2281 has two parallel panels 2281a and 2281b made of transparent radioprotective material such as lead-containing plastic, of the type "Kyowaglass" (registered trademark), radioprotective plastic of the type "Novashield glass" (registered trademark), lead-containing glass, or others, all having a lead equivalence comprised between 0.2 mm and 3 mm, which are spaced apart at a distance corresponding, to within a clearance, to the thickness of the panel forming the lower part 2272 of the upper panel 227.

Both parallel panels 2281a and 2281b are assembled by spacer profiles provided on their respective vertical lateral edges and their horizontal lower edge.

These two parallel panels 2281a and 2281b, which form the upper part 2281, sandwich panel 2271 and they are configured for moving translationally vertically with respect to said panel 2272, in order to obtain the telescopic feature of the upper part 22 of the front wall structure 2 and to be adjustable in height.

To this end, the lower panel 228 is hanged on said upper panel 227 by means of an equilibrium system, here by two lateral spiral springs 229 of the type with constant force.

These spiral springs 229 are mounted on the sides of the upper panel 227 and of the lower panel 228. They consist of a metal band, —one end of which is rolled to form a spiral and is fixed to the upper panel 227 (around an axle that extends perpendicularly to the plane of said panel 227), —and the other end of which is fixed to the board of the lateral edge turned to the lower panel 228.

The strength of the equilibrium system 229 is adapted for allowing an operator to manually perform the upward and downward movements of the lower panel 228 with respect to the upper panel 227. As a result of the constant force of the springs 229, panel 228 remains in its position, once it has been moved.

FIGS. 1, 2, 4, 7 (in dotted lines), and 8-10 represent panel 228 in the maximum upper position; FIGS. 7, 11, and 12 represent panel 228 in the maximum lower position.

The lower part 2282 of the lower panel 228 is constituted by a flexible curtain formed by a juxtaposition of a plurality of flexible strips made of radioprotective material. The upper edge of the flexible curtain 2282 is fixed to the lower edge of the upper part 2281; and its lower edge forms the lower edge 224 of the pivotal upper part 22.

Here, it is to be noticed that this lower edge 224 has the shape of a circular arc, in order to follow the general outline of a patient lying on an examination table.

As a variant, that lower edge 224 may be straight.

This flexible curtain 2282 can extend over a height of some centimeters or tens of centimeters. It is, for example, made of radioprotective material such as PVC or rubber which contains radioprotective material and which has a lead equivalence of at least 0.125 mm.

The flexible curtain 2282 may be positioned such as to have contact with the body of a patient lying on an examination table, in order to optimize the radioprotection; it also allows passing the arms of the operator if he wants to intervene on the other side of the pivoting upper part 22.

The upper edge 223 of the upper part 22 of the front wall structure 2 comprises an extension which forms a roof 16 made of radioprotective material and which extends on the side of the inner face 225.

Here, that extension 16 extends perpendicularly to the plane of the front wall structure 2 and over the whole width of the upper edge 223; it is advantageously made of transparent material, for example of lead-containing plastic, of the type "Kyowaglass" (registered trademark), radioprotective plastic of the type "Novashield glass" (registered trademark), lead-containing glass, or others, all having a lead equivalence comprised between 0.2 mm and 3 mm.

The extension forming roof 16 extends in a plane offset with respect to the plane of the extension forming roof 14 of the lateral wall structure 3, in order to not affect pivoting of the pivoting part 22.

The shape and the dimensions of these two extensions forming roof 14 and 16 are adapted for obtaining a partial overlapping and, thus, for obtaining a continuous radioprotection, whatever the allowed position of the pivoting upper part 22 might be.

Figure 5:
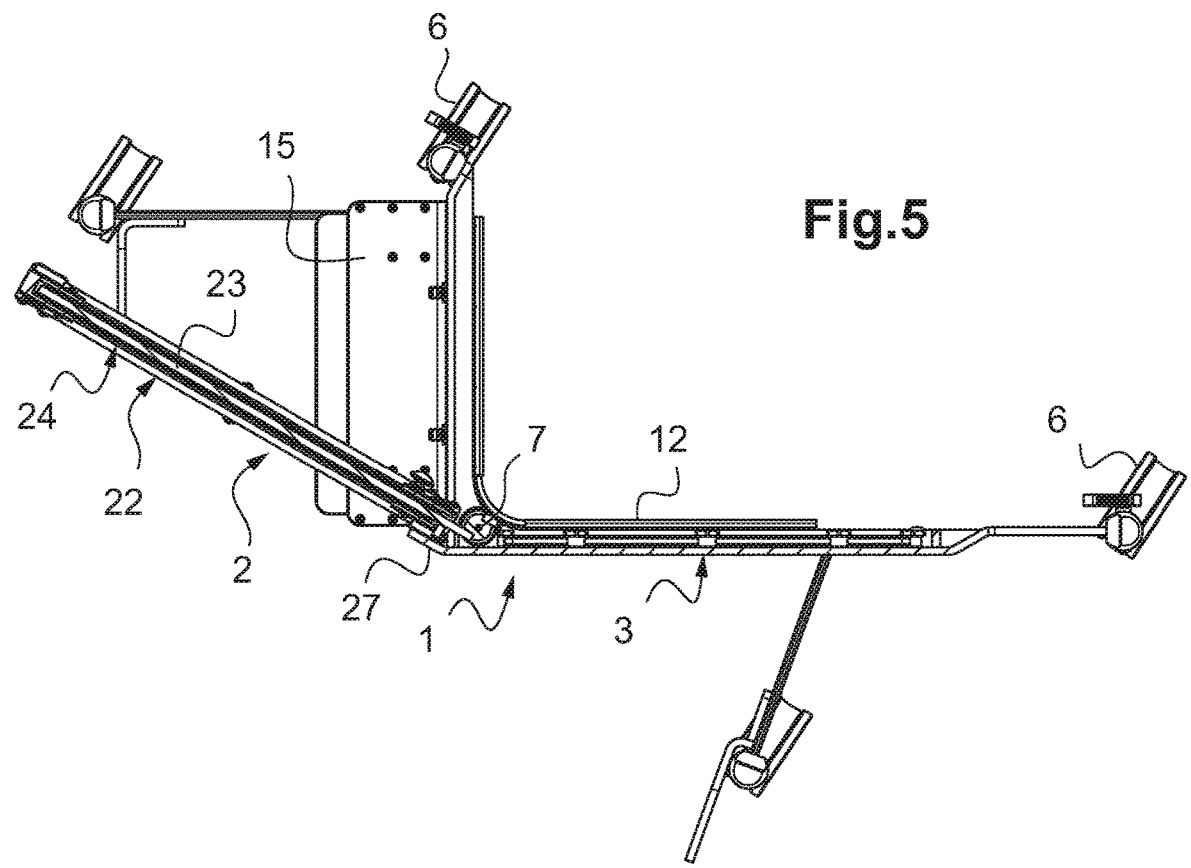
FIG. 5 is a sectional view of the radioprotective screen according to plane 5-5 of FIG. 4.
Figure 6:
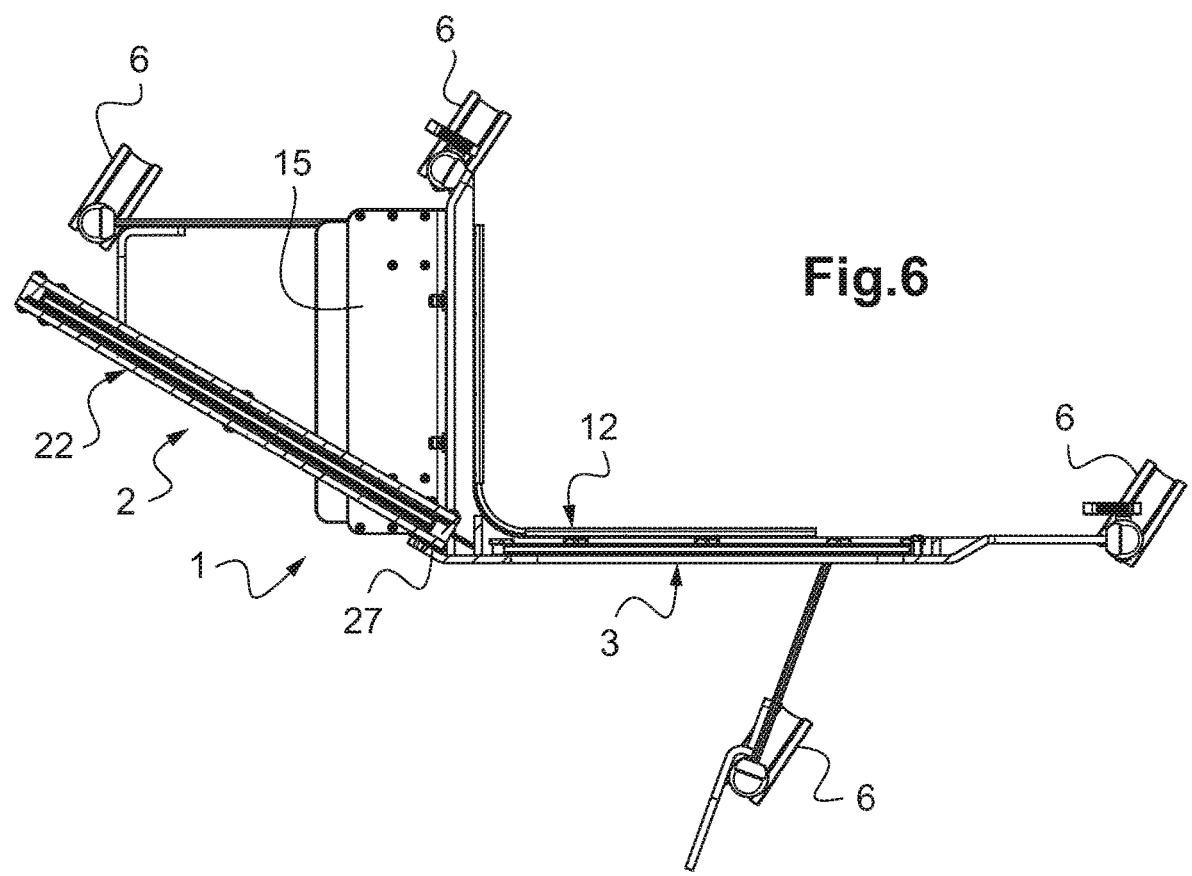
FIG. 6 is a sectional view of the radioprotective screen according to plane 6-6 of FIG. 4.

The upper part 22 of the front wall structure 2 is mounted pivotally around the pivoting axis 7 on the corner edge 4 by means of an arm 23 shown on FIGS. 5, 11, and 12.

This arm 23 consists of a flat element made of steel, which extends horizontally from the upper part of the corner edge 4.

One of the ends of arm 23 is mounted articulated around the vertical pivoting axis 7 with respect to the lateral edge 32 of the lateral wall structure 3; and this arm 23 is inserted in a reception space 24 formed in the upper part 2271 of the upper panel 227 of the pivoting part 22, leading out laterally in order to serve as a support for the assembly formed by the upper panel 227, the lower panel 228, and the extension forming roof 16.

That assembly formed by the upper panel 227, the lower panel 228, and the extension forming roof 16 is mounted movably for horizontal translation on the supporting arm 23 for taking:

a so-called active position in which the lateral edge 222 of the pivoting upper part 22 is located as close as possible to the lateral edge 32 of the lateral wall structure 3 (as illustrated on FIGS. 1 to 7), and a so-called inactive position in which the lateral edge 222 of the pivoting upper part 22 is located at a distance from the lateral edge 32 of the lateral wall structure 3 (as illustrated on FIGS. 11 and 12), allowing for fixing a sterile-cover equipment, as explained hereafter.

The upper part of the reception space 24 is advantageously provided with rollers 26 (shown on FIG. 10) which are arranged for rolling on the upper edge of the support arm 23 and for facilitating corresponding sliding operations for taking the afore-mentioned active and inactive position.

Means can also be foreseen for locking releasably the aforementioned active and inactive position. Those means, which are not shown on the figures, may consist of an indexing system, for example of the type of a ball (or of balls) mounted on a spring and supported by one of the elements, and cooperating with a housing formed on the other element.

On FIGS. 1-7, it can be seen that the lateral edge 32 of the upper part 38 of the lateral wall structure 3, which forms part of the corner edge 4, comprises an extension having the shape of a lateral wing 27 that extends over a width of some centimeters. That lateral wing 27 is configured for covering the lateral edge 222 in front of the upper part 22 of the front wall structure 2, and the associated pivoting axis 7, when this upper part 22 is in the active position, and this on the side of the outer face 226 of the upper part 22, in order to optimize the radioprotection of screen 1.

As an indication, only, the height of screen 1, i.e. the distance between the supporting plane at the ground for the rollers 6 and the extensions forming roof 14, 16, may be in the order of 1.90 to 2.30 m. The width of the lateral wall structure 3 and the one of both parts 21 and 22 of the front wall structure 2 may be smaller than or equal to 0.80 m, for example in the order of 0.60 to 0.80 m; and the upper edge 214 of the lower part 21 of the front wall structure 2 may extend at a height of about 0.70 to 1.10 m.

The upper part 22 of the front wall structure 2 is mounted pivotally around the pivoting axis 7 between:

a so-called closed position, illustrated on FIG. 7, in which that upper part 22 extends in a plane parallel or essentially parallel to the plane in which the lower part 21 extends, as an extension or essentially as an extension of the latter, and a position of maximum opening, illustrated on FIGS. 1 to 6, in which that upper part 22 extends in a plane offset on the side of the outer face 216 of the lower part 21.

The corresponding angular pivoting sector a (FIG. 3) may be comprised between 50 and 90°, for example in the order of 60°.

In the context of using said radioprotective screen 1 in an operating room, certain ones of the parts which constitute the screen, are covered by a sterile-cover equipment 40 such as illustrated on FIG. 12.

This sterile-cover equipment 40 is configured for covering at least part of the height of the inner and the outer face of the radioprotective screen 1, and here it comprises:

a cover part 401 configured for covering the upper part 22 of the front wall structure 2 at least partially, a cover part 402 configured for covering, at least partially, the lateral wall structure 3 and the lower part 21 of the front wall structure 2, and a cover part 403 as a flexible structure configured for covering, at least partially, the protective extension shaped as a tablet 15, fixed or not to the afore-mentioned cover part 402.

The cover part 401 is configured for covering the lower panel 228 of the pivoting upper part 22. It is in the form of a flexible envelope or pocket made of transparent material, for example a transparent sheet of polypropylene having an overall square or rectangular shape, one edge of which being provided with a positioning opening 401a.

After the upper part 22 has been moved into the inactive position, such as illustrated on FIGS. 11 and 12 (i.e. with its lateral edge 222 separated from the lateral edge 32 of the lateral wall structure 3), the flexible pocket 401 is positioned by introducing the lower edge 224 of the upper part 22 into the opening 401a; and once the flexible pocket 401 is correctly positioned around the lower panel 228, appropriate fixing means of the type of adhesive bands, suction cups, elastic bands or others make sure that it remains in that position.

Such a positioning is made possible by putting the upper part 22 of the radioprotective screen 1 in the inactive position. It is clear that it has to be put back into the active position, when it has to be used.

The cover part 402 consists of at least one panel made of flexible material adapted for covering part of the height of the lower parts 21 and 37 of the front wall structure 2 and the lateral wall structure 3 as well as part of the height of the upper part 38 of the lateral wall 3.

Here, the cover part 402 consists of a single panel constituted of an assembly of several panels made of different materials, namely a panel 402a made of transparent material, for example of polypropylene intended to be positioned in front of the transparent part 381 of said lateral wall structure 3, and a panel 402b made of non-transparent, non-woven material, for example of polypropylene, intended to be positioned on said lower parts 21 and 37 of the front wall structure 2 and the lateral wall structure 3.

Positioning of that cover part 402 is done by simply covering the respective zones of radioprotective screen 1. In order to simplify the beginning of that operation, the material panel 402 may comprise a hooking structure on one end edge, configured for hooking on a hooking structure 271 foreseen on base 8 of screen 1, for example at the height of the covering wing 27.

Once that cover part 402 is correctly positioned, appropriate fixing means of the type of adhesive bands, suction cups, elastic bands or others make sure that it remains in that position.

The cover part 403, which is configured for covering the protective extension in the form of tablet 15, may have the form of an extension that is fixed to the afore-mentioned cover part 402 provided with appropriate fixing means of the type of adhesive bands, suction cups, elastic bands or others making sure that it remains in that position.

As a variant, that cover part 403 may have the form of an independent envelope or pocket made of flexible material, for example of polypropylene, having an overall rectangular shape with one edge being provided with a positioning opening.

Then, this flexible pocket 403 is positioned by introducing the end of the protective extension in the form of tablet 15 into its opening; and once correctly positioned, appropriate fixing means of the type of adhesive bands, suction cups or others make sure that it remains in that position.

Figure 13:
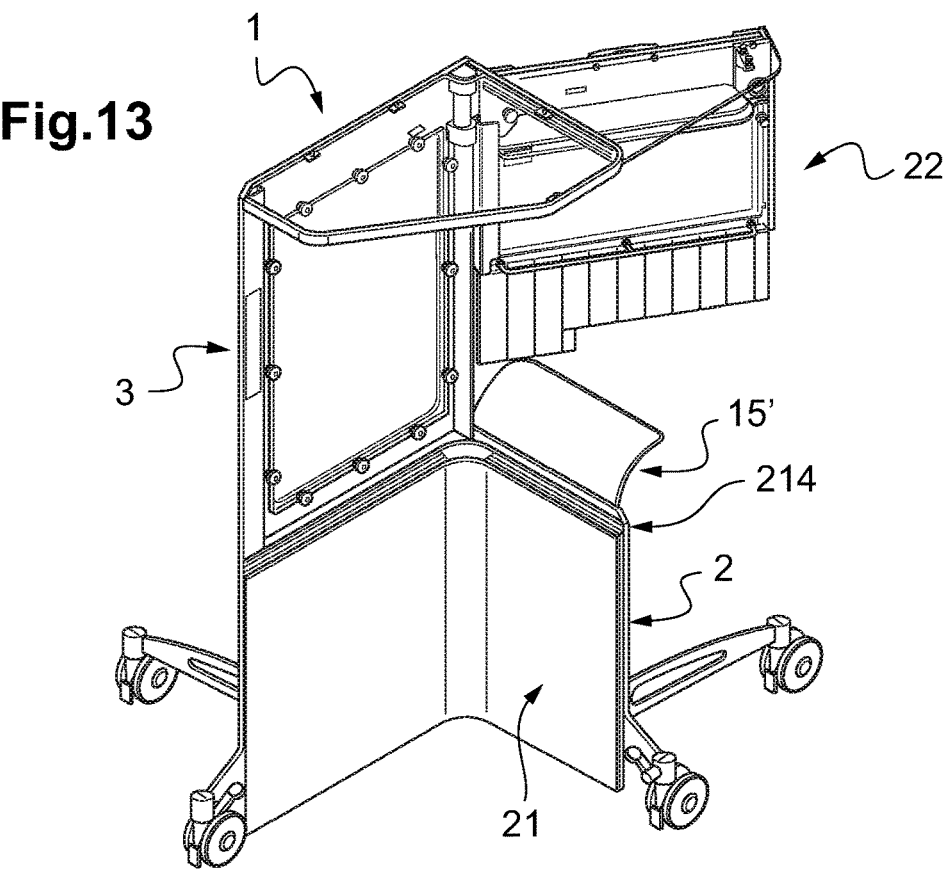
FIG. 13 is a perspective view of a variant of an embodiment of the radioprotective screen according to the invention.
Figure 14:
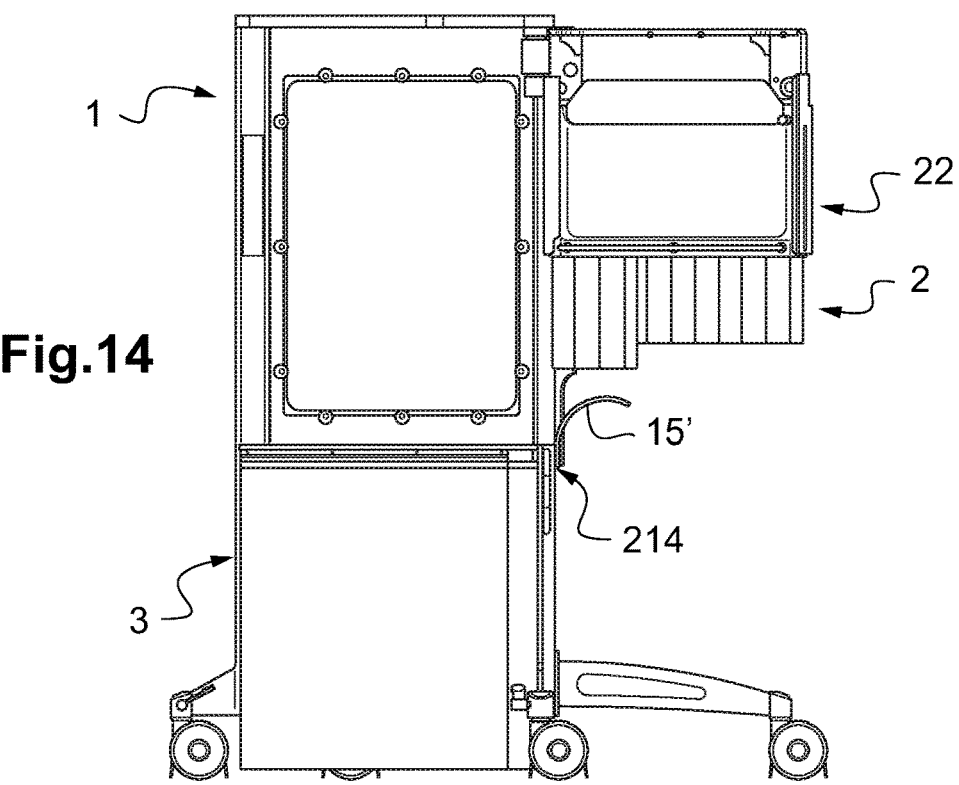
FIG. 14 is a side view of the radioprotective screen of FIG. 13.

Still as a variant, the tablet 15 illustrated with the embodiment of FIGS. 1 to 12, may be replaced by a semi-rigid bib such as shown on FIGS. 13 and 14.

As can be seen on these FIGS. 13 and 14, the semi-rigid bib 15' extends upwards from the upper edge 214 of the lower part 21 of the front wall structure 2 and cantilevered to the side of the outer face 216.

It consists of a one-piece panel made of radioprotective material (for example lead-containing PVC or rubber or another radioprotective material) which is fixed along the upper edge 214 and the cantilevered edge of which is free.

At rest, that bib 15' has a curved or circular-arc shaped cross-section. Since it is semi-rigid, its shape and its positioning may be voluntarily modified by the operator or due to a contact with an appliance or an element of the surroundings (patient, supporting table for the patient, . . . ).

The radioprotective screen 1 according to the invention is particularly adapted for protecting one or several operators in an operating room containing one or several appliances emitting ionizing radiation, especially a fluoroscopic appliance.

This radioprotective screen 1 can easily be moved by simply rolling it on the ground, in order to correctly position its front wall structure 2 and lateral wall structure 3 between the operator and the ionizing radiation emitting appliance.

As shown on FIG. 2, it may be positioned as close as possible to an examination table T on which a patient is lying, its front wall structure 2 being situated along that table T.

Then, the operator can manually move the pivoting upper part 22 and the vertically translationally moving part 228, in order to make his manipulations comfortable and to optimize the radioprotection depending on the intervention he has to perform on the patient.

Especially, it is clear that pivoting the pivoting upper part 22 to the front side allows assuring an efficient radioprotection, the flexible curtain 2282 being in contact with the patient, and making free a large opening above the patient, in front of the lower part 21 of the front wall structure 2, facilitating the intervention of the operator.

There is no interaction between the movable screen on wheels and the patient; it also allows the operator to intervene on the patient in an urgency situation.

On the other hand, it also is clear that the contact of certain movable parts of the equipment (for example the arc of the fluoroscopic equipment) with the flexible panel 12 or with the pivoting upper part 22, does not entail any major perturbation of the overall positioning of radioprotective screen

The invention claimed is:

1. A radioprotective screen for protecting at least one operator from ionizing radiation, said screen comprising:
a front wall structure made of radioprotective material and a lateral wall structure made of radioprotective material linked to one another at a vertical or essentially vertical corner edge,
said front wall structure comprising a lower part and an upper part configured to be moved relative to one another, said upper part of said front wall structure being mounted pivotally around a vertical or essentially vertical pivoting axis at said corner edge, said lower part of the front wall structure extending in a vertical or essentially vertical plane which is offset with respect to the plane of said lateral wall structure by a fixed angle between 70° and 120°, the lower part of the front wall structure being defined by
a free lateral edge,
a lateral edge defining a part of said corner edge, a lower edge, and
an upper edge,
the lateral wall structure extending in a vertical or essentially vertical plane, the lateral wall structure comprising
a free lateral edge,
a lateral edge defining a part of said corner edge,
a lower edge,
an upper edge,
an upper part, at least a portion of the upper part being made of transparent radioprotective material, and
a lower part;
a base provided with ground support wheels; and
a part made of flexible radioprotective material which is shaped as a panel that extends over a part of the height of said corner edge, from the lower edge of the lower part of the lateral wall structure, and from the lower edge of the lower part of the front wall structure, over a part of said lower part of the lateral wall structure and over a part of the lower part of the front wall structure at both sides of said corner edge.

2. The screen according to claim 1, wherein said panel made of flexible radioprotective material extends from the lower edge of said lower part of the lateral wall structure and from the lower edge of the lower part of the front wall structure, over more than half of the height of said lower parts of the lateral wall structure and the front wall structure, the panel extending from said corner edge, over more than half of the width of said lower parts of the front wall structure and the lateral wall structure.

3. The screen of claim 1, wherein said lower part of the front wall structure extends in the vertical or essentially vertical plane which is offset with respect to the plane of said lateral wall structure by the fixed angle on the order of 90°.

4. The screen according to claim 1, wherein the lateral wall structure further comprises
an inner face turned towards a positioning space of the operator, and
an opposite outer face opposite the inner face, and
wherein the upper edge of the lateral wall structure comprises an extension forming a roof made of radioprotective material, which extends on the side of said inner face.

5. The screen according to claim 1, wherein the lower part of the front wall structure comprises
an inner face turned towards a positioning space of the operator,
an opposite outer face opposite the inner face, and
an upper edge comprising a protective extension shaped as a tablet or a semi-rigid bib and made of a radioprotective material which extends on the side of said outer face.

6. A radioprotective screen for protecting at least one operator from ionizing radiation, said screen comprising:
a front wall structure made of radioprotective material and a lateral wall structure made of radioprotective material linked to one another at a vertical or essentially vertical corner edge,
said front wall structure comprising a lower part and an upper part configured to be moved relative to one another, said upper part of said front wall structure being mounted pivotally around a vertical or essentially vertical pivoting axis at said corner edge,
the lower part of the front wall structure comprising
an inner face turned towards a positioning space of the operator,
an opposite outer face opposite the inner face, and
an upper edge including a protective extension shaped as a tablet or a semi-rigid bib and made of a radioprotective material which extends on the side of said outer face; and
a base provided with ground support wheels.

7. The screen according to claim 6, wherein said tablet extends in a horizontal or essentially horizontal position from the upper edge of the lower part of the front wall structure,
wherein said tablet is mounted pivotally on said upper edge of the lower part of the front wall structure, in order to allow the tablet to be raised from said horizontal position, and
wherein said tablet comprises a retractable end extension configured to make the tablet telescopic.

8. A radioprotective screen for protecting at least one operator from ionizing radiation, said screen comprising:
a front wall structure made of radioprotective material and a lateral wall structure made of radioprotective material linked to one another at a vertical or essentially vertical corner edge,
said front wall structure comprising a lower part and an upper part configured to be moved relative to one another, said upper part of said front wall structure being mounted pivotally around a vertical or essentially vertical pivoting axis at said corner edge, the upper part of the front wall structure being formed by at least one panel made of radioprotective material, the upper part of the front wall structure comprising
a free lateral edge,
a lateral edge forming a part of the corner edge,
an upper edge,
a lower edge,
an inner face turned towards a positioning space of the operator, and
an opposite outer face opposite the inner face,
the lateral wall structure including a lateral edge forming a part of said corner edge, the lateral edge comprising an extension shaped as a lateral wing configured to cover the lateral edge of the front wall structure that is in front of the upper part of the front wall structure, and the associated pivoting axis, the lateral wing being formed on the side of the outer face of the upper part of the front wall structure; and
a base provided with ground support wheels.

9. A radioprotective screen for protecting at least one operator from ionizing radiation, said screen comprising:
a front wall structure made of radioprotective material and a lateral wall structure made of radioprotective material linked to one another at a vertical or essentially vertical corner edge,
said front wall structure comprising a lower part and an upper part configured to be moved relative to one another, said upper part of said front wall structure being mounted pivotally around a vertical or essentially vertical pivoting axis at said corner edge, the upper part of the front wall structure being formed by at least one panel made of radioprotective material, the upper part of the front wall structure comprising
a free lateral edge,
a lateral edge forming a part of the corner edge, an upper edge, a lower edge, an inner face turned towards a positioning space of the operator, and an opposite outer face opposite the inner face, the lateral wall structure comprising an inner face turned towards the positioning space of the operator, and an opposite outer face opposite the inner face of the lateral wall structure, the upper edge of the lateral wall structure comprising an extension forming a roof made of radioprotective material, which extends on the side of said inner face of the lateral wall structure, the upper edge of the upper part of the front wall structure comprising a roof-forming extension made of radioprotective material which extends on the side of the inner face of said upper part of the front wall structure in a plane that is offset with respect to the plane of the roof-forming extension of the lateral wall structure; and a base provided with ground support wheels.

10. A radioprotective screen for protecting at least one operator from ionizing radiation, said screen comprising:

a front wall structure made of radioprotective material and a lateral wall structure made of radioprotective material linked to one another at a vertical or essentially vertical corner edge, said front wall structure comprising a lower part and an upper part configured to be moved relative to one another, said upper part of said front wall structure being mounted pivotally around a vertical or essentially vertical pivoting axis at said corner edge, the upper part of the front wall structure being formed by at least one panel made of radioprotective material, the upper part of the front wall structure comprising a free lateral edge, a lateral edge forming a part of the corner edge, an upper edge, a lower edge, an inner face turned towards a positioning space of the operator, an opposite outer face opposite the inner face, an upper panel at least a part of which is made of radioprotective material, and a lower panel at least part of which is made of a transparent radioprotective material, said lower panel being vertically translationally movable with respect to said upper panel, in order to form a telescopic upper part of the front wall structure, the height of which is adjustable; and a base provided with ground support wheels.

11. The screen according to claim 10, wherein the lower edge of the upper part of the front wall structure is formed by a flexible curtain composed by a juxtaposition of a plurality of flexible bands made of radioprotective material.

12. The screen according to claim 10, wherein the movable lower panel is attached to said upper panel by an equilibrium system.

13. The screen according to claim 12, wherein the equilibrium system is of a spiral-spring type with constant force.

14. A radioprotective screen for protecting at least one operator from ionizing radiation, said screen comprising:

a front wall structure made of radioprotective material and a lateral wall structure made of radioprotective material linked to one another at a vertical or essentially vertical corner edge, said front wall structure comprising a lower part and an upper part configured to be moved relative to one another, said upper part of said front wall structure being mounted pivotally around a vertical or essentially vertical pivoting axis at said corner edge, the upper part of the front wall structure being formed by at least one panel made of radioprotective material, the upper part of the front wall structure comprising a free lateral edge, a lateral edge forming a part of the corner edge, an upper edge, a lower edge, an inner face turned towards a positioning space of the operator, an opposite outer face opposite the inner face, a supporting arm pivotally mounted on said corner edge around said pivoting axis, and at least one panel is movably mounted on said supporting arm for horizontal translational movement.

15. Cover-shaped equipment configured to cover at least part of the height of the radioprotective screen according to claim 14, the cover-shaped equipment comprising:

a flexible pocket provided with an opening, said flexible pocket being configured to at least one partially cover the upper part of the front wall structure by entering the lower edge of the front wall structure into the opening of said flexible pocket, said flexible pocket being provided with at least one transparent part and with a fixing system configured to fix the at least one transparent part to said upper part of the front wall structure; and at least one flexible panel configured to at least partially cover said lateral wall structure and the lower part of said front wall structure, said at least one flexible panel comprising at least one transparent part configured to be positioned in front of the transparent part of said lateral wall structure, and a fixing system on said lateral wall structure and said front wall structure; and a flexible structure at least partially covering a tablet that extends along the upper edge of the lower part of the front wall structure, the flexible structure being either fixed to said panel to cover said lateral wall structure and the lower part of the front wall structure, or independent from said panel, said flexible structure being provided with a fixing system configured to fix the flexible structure to said tablet.

* * * * *